United States Patent [19]

Mallia et al.

[11] Patent Number: 5,538,858
[45] Date of Patent: * Jul. 23, 1996

[54] RAPID ASSAY FOR RADIOACTIVE DETERMINATION OF PROTEIN KINASE ACTIVITY

[75] Inventors: A. Krishna Mallia, Rockford; Keld Sorensen, Roscoe, both of Ill.

[73] Assignee: Pierce Chemical Company, Rockford, Ill.

[*] Notice: The portion of the term of this patent subsequent to Apr. 8, 2014, has been disclaimed.

[21] Appl. No.: 225,469

[22] Filed: Apr. 8, 1994

[51] Int. Cl.$^6$ .............................. C12Q 1/48; A61K 51/00
[52] U.S. Cl. .................... 435/15; 435/4; 435/21; 435/194; 436/504; 436/804
[58] Field of Search .................. 435/15, 4, 21, 435/194; 436/504, 804; 424/1.1

[56] References Cited

U.S. PATENT DOCUMENTS

| | | | |
|---|---|---|---|
| 4,923,802 | 5/1990 | Gallis | 435/15 |
| 5,141,852 | 8/1992 | Egan et al. | 435/15 |
| 5,215,888 | 6/1993 | Shalteil et al. | 435/15 |

OTHER PUBLICATIONS

Toomik et al, *Analytical Biochemistry*, vol. 209, pp. 348–353, 1993.

Casnellie et al, *Methods in Enzymology*, vol. 200, pp. 115–120, 1991.

Sigma Catalog—*Biochemicals and Organic Compounds for Research and Diagnostic Reagents*, pp. 1072–1073, and pp. 854–857, 1993.

*Primary Examiner*—Michael G. Wityshyn
*Assistant Examiner*—Abdel A. Mohamed

[57] ABSTRACT

A rapid radioactive method of measuring enzymatic activity of a protein kinase is disclosed. The method is an improvement to existing methodology which involves phosphorylating a peptide substrate using $^{32}$P-ATP, adsorbing the phosphorylated peptide to a solid phase, washing the phase to remove non-adsorbed $^{32}$P-ATP, and measuring the radioactivity of the phosphorylated peptide adsorbed to the phase. The disclosed improvement uses a membrane as the solid phase and positions the membrane within a chamber to separate the chamber into a first and second region. Washing is accomplished with centrifugal force; the washed solution being forced through the membrane from the first region into the second region.

12 Claims, 1 Drawing Sheet

U.S. Patent      Jul. 23, 1996      5,538,858
FIG. 1
FIG. 2
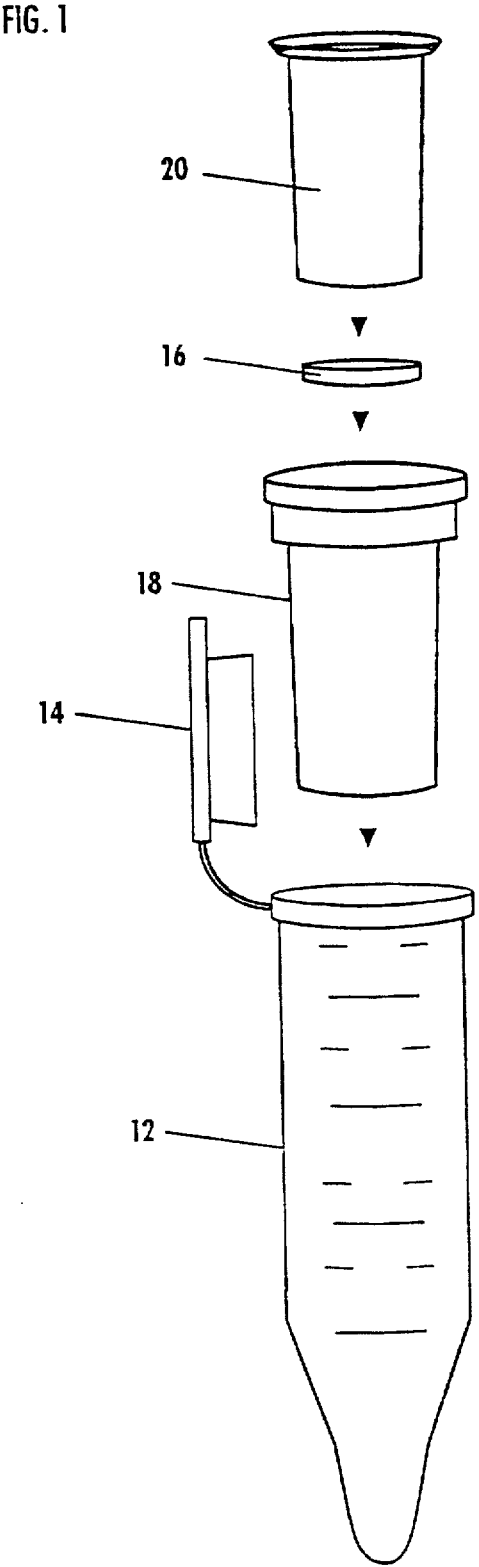
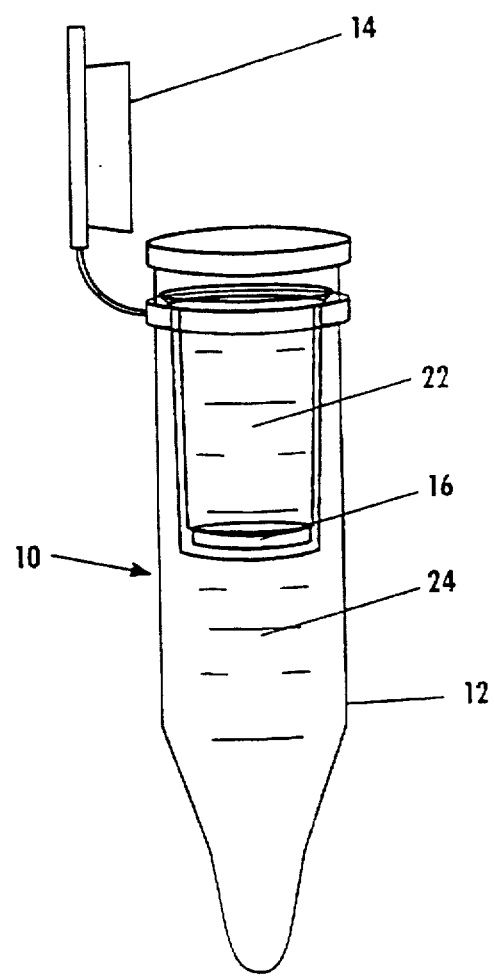

5,538,858

RAPID ASSAY FOR RADIOACTIVE DETERMINATION OF PROTEIN KINASE ACTIVITY

FIELD OF THE INVENTION

The present invention relates to techniques for assaying enzymatic activity by a radioactive technique and, more particularly, to a rapid radioactive method for measuring the activity of Protein Kinases.

BACKGROUND OF THE INVENTION

Protein Kinases are enzymes which covalently modify proteins and peptides by the attachment of a phosphate group to one or more sites on the protein or peptide. The measurement of Protein Kinase activity is important since studies have shown that these enzymes are key regulators of many cell functions.

The most widely used technique for measuring Protein Kinase activity is based on radioactive detection. In this method, a sample containing the kinase of interest is incubated with activators and a substrate in the presence of gamma $^{32}$P-ATP. After a suitable incubation period, the reaction is stopped and an aliquot of the reaction mixture is placed directly onto a filter which binds the substrate. The filter is then washed multiple times to remove excess radioactivity, and the amount of radiolabelled phosphate incorporated into the substrate is measured by scintillation counting.

This method is widely used and provides an accurate method for determining Protein Kinase activity in both crude and purified samples. However, because of the necessity of multiple washings, which are generally done by manually transferring the filter to a beaker and washing and rinsing with gentle agitation, the procedure is quite time consuming.

Other methods for detecting kinase activity are based on separations due to the charge differences between phosphorylated and non-phosphorylated proteins and peptides. In these respects, techniques based on gel electrophoresis and HPLC have, among others, been used. In combination with these techniques, spectrophotometric and fluorometric detection have been used. Reference is made to International Patent Application WO 93/10461 and U.S. Pat. Nos. 5,120, 644 and 5,141,852 for descriptions of many methods heretofore used for detecting protein kinase activity. Also reference is directed to *Analytical Biochemistry*, 209, 348–353, 1993, "Protein Kinase Assay Using Tritiated Peptide Substrates and Ferric Adsorbent Paper for Phosphopeptide Binding."

SUMMARY OF THE INVENTION

The present invention provides an improvement in the radioactive method of measuring enzymatic activity of a protein kinase, such as Protein Kinase A, Protein Kinase C, and tyrosine kinases. The general method to which the improvement of the present invention is directed comprises (1) phosphorylating a peptide substrate in an aqueous medium in the presence of a radioactive phosphoryl donor compound and the enzyme, (2) while in said aqueous medium, adsorbing the radioactive phosphorylated peptide to a solid phase, (3) washing the solid phase with a wash solution to remove unreacted radioactive phosphoryl donor compound and (4) measuring the radioactivity of phosphorylated peptide adsorbed to the solid phase. The improvement to the foregoing method provided by this invention involves, first, using as the solid phase a membrane positioned within a chamber which separates the chamber into discrete first and second regions and, second, accomplishing the washing step by passing, with applied external force, the wash solution through the membrane from the first region to the second region. The improvement contributed by this invention increases the speed with which the assay can be accomplished. Also, radioactive waste is minimized and handling is facilitated.

BRIEF DESCRIPTION OF DRAWING

FIG. 1 illustrates the component parts of a unit which can be used in accomplishing the assays described herein;

FIG. 2 illustrates, in assembled form, the unit referred to above.

DETAILED DESCRIPTION OF INVENTION

Referring to the drawings, FIGS. 1 and 2 depict a unit which can be used in accomplishing the assay described herein. In particular, the unit is useful in those aspects of the assay described herein wherein radioactive phosphorylated peptide is separated from radioactive phosphoryl donor compound by washing to remove the non-adsorbed donor.

The depicted unit 10 includes a tube 12 generally of a shape such that it can be accommodated in the receptacles of conventional centrifuges. A cap 14 is provided to enclose the tube when desired. For the purpose of housing a membrane 16 within the tube 12, a bucket 18 is provided. As shown in FIG. 2, in assembled fashion, the membrane 16 rests flatly on the bottom surface of the bucket 18 and is held in place by the sleeve 20. While not specifically illustrated, the bottom surface of the bucket 20 is perforated to permit the passage of wash solution through the membrane and bottom surface.

As shown, the membrane 16 separates the chamber within the tube 12 into two discrete regions; a first region 22 being the interior of the bucket 18 and the second region 24 being the volume of the chamber not occupied by the bucket. In use, wash solution placed in the first region 22 is forced through the membrane 16 and into the second region 24. The force to accomplish this is preferably applied centrifugally by use of a centrifuge.

Turning to the membrane 16, phosphocellulose paper, such as P81 from Whatman, can be used. The assay is accomplished conventionally, except with respect to the manner of washing free radioactive donor compound, typically $^{32}$P-ATP, from the membrane. As indicated, this is accomplished by forcing the wash solution, using applied force, preferably centrifugal, through the membrane. The result is that the washing time necessary to achieve acceptable background levels is reduced, as is handling of the radioactive membrane. In this latter aspect, after washing, the bucket can be directly transferred to a scintillation vial without membrane removal.

The following examples illustrate the present invention. All parts and percentages are by weight unless otherwise indicated. In Examples I & II, and in accordance with the present invention, membranes were prepared by cutting small circles (8 mm diameter) out of phosphocellulose paper obtained from Whatman under their designation P81 paper. Using the tube and bucket arrangement depicted in the drawings, the membranes were inserted into the illustrated buckets thus covering the perforated bottom surface of the buckets. Thereafter, insertion of the sleeve holds the membranes in place.

EXAMPLE I (Protein Kinase C)

To perform the assay for Protein Kinase C, a commercially available assay system for this enzyme, available from Amersham International plc in kit form as Code RPN77, was used. The Amersham kit contained the following constituents:

Calcium Buffer (12 mM calcium acetate in 50 mM Tris, pH 7.5)
Lipid Buffer (8 mole % L-alpha Phosphatidyl-L-serine and 24 μg/ml phorbol 12-myristate 13-acetate in 50 mM Tris, pH 7.5)
Peptide Buffer (900 μM peptide-RKRTLRRL, EGF receptor—in 50 mM Tris buffer, pH 7.5)
DTT Buffer (30 mM dithiothreitol in 50 mM Tris buffer)
ATP Buffer (150 μM ATP and 45 mM magnesium acetate in 50 mM Tris buffer)

Radioactive gamma-$^{32}$P-ATP ($^{32}$P-ATP) was also obtained from Amersham and used in accordance with the instructions for the assay (4 μl of $^{32}$P-ATP was added to 500 μl of the ATP buffer contained in the kit).

In accomplishing the assay in accordance with the present invention, equal volumes of the Calcium, Lipid, Peptide and DTT buffers were mixed. A reaction solution was then formed by combining 25 μl of the mixture with 25 μl of $^{32}$P-ATP solution and 25 μl of Protein Kinase C sample. The reaction proceeded for 15 minutes at room temperature and was then terminated by the addition of 100 μl 75 mM phosphoric acid.

25 μl of the reaction mixture so formed was pipetted onto the phosphocellulose membrane contained in buckets, and the buckets inserted into micro centrifugation tubes. Using a conventional centrifuge, the tubes were spun at 13,500 rpm for 30 seconds. Thereafter, 500 μl of 75 mM phosphoric acid was added to each bucket and the tubes again spun at 13,500 rpm for 30 seconds. This washing step was then repeated a second time after which the buckets were removed from the tubes, and each bucket was transferred, intact, to a scintillation vial containing 10 ml scintillant liquid (Ecoscint, obtained from Fisher Scientific). Radioactive counting was performed using an LKB scintillation counter set to count $^{32}$P.

Using the above assay protocol, a solution of Protein Kinase C was serially diluted and the activity of $^{32}$P-ATP labeled peptide measured (in triplicate for each). The total radioactivity applied was determined by measuring the radioactivity of a blank sample (no enzyme) that was applied to the membrane and washing and centrifuging omitted. This total was 192,990 counts per minute (CPM) with a coefficient of variation of 1.4%. Table I presents the results of these assays.

TABLE I

| Dilution of Enzyme Sample | mean cpm | CV value |
| --- | --- | --- |
| None | 68321 | 2.8% |
| 3 | 29209 | 2.0% |
| 5 | 14192 | 0.4% |
| 10 | 8466 | 6% |
| 100 | 738 | 18% |

When plotting these values, a linear regression coefficient of better than 0.99 is obtained. This data shows that an assay in accordance with this invention yields very low CV values which may be partly due to the "fixed" configuration during counting, where the paper cannot "curl" as in the traditional method.

The efficiency of washing unbound $^{32}$P-ATP from the membrane using the method of the present invention was compared with a conventional technique as described by Amersham. This latter technique, rather than using membranes with forced washing, utilized 2.5 cm squares of P81 phosphocellulose paper. Five washing steps were used, each step being 10 minutes with intermittent gentle mixing using a platform shaker set at low speed. To measure washing efficiency, no Protein Kinase C was included and two samples of $^{32}$P-ATP with different total CPM's were utilized. The results, set forth in Table II, were as follows.

TABLE II

| | After Washing | |
| --- | --- | --- |
| Initial Counts | Current Invention | Conventional |
| 188266 cpm | 556 cpm | 834 cpm |
| 192990 cpm | 225 cpm | 618 cpm |

As shown, background radioactivity can be reduced by using the method of the present invention.

EXAMPLE II (Protein Kinase A)

To perform the assay for Protein Kinase A, a magnesium chloride-ATP buffer (see Example VI) was rendered radioactive by the addition of 1 μl of $^{32}$P-ATP per 100 μl of buffer. 5 μl of this radioactive buffer, 5 μl of an activator solution (500 μM c-AMP in water) and 5 μl of Kemptide solution (1 mg/ml Kemptide-LRRASLG, amino acid sequence) were added to 10 μl Protein Kinase A sample. After 15 minutes incubation, the reaction was quenched by addition of 35 μl 75 mM phosphoric acid.

Application to a phosphocellulose membrane in a bucket and subsequent washing follows the Example I protocol. Preparation of a standard curve as described with respect to Example I indicates that the assay is linear with a regression coefficient of 0.994.

What is claimed is:

1. In a radioactive method of measuring enzymatic activity of a protein kinase, comprising: (1) phosphorylating a peptide substrate in an aqueous medium in the presence of a radioactive phosphoryl donor compound and the enzyme, (2) while in said aqueous medium, adsorbing the radioactive phosphorylated peptide to a solid phase, (3) washing the solid phase containing adsorbed radioactive phosphorylated peptide with a wash solution to remove unreacted radioactive phosphoryl donor compound, and (4) measuring the radioacitvity of the phosphorylated peptide adsorbed to said solid phase, the improvement wherein said solid phase is a membrane positioned within a chamber which separates the chamber into discrete first and second regions, and said washing is accomplished by passing, with applied force, said wash solution through the membrane from said first region into said second region.

2. The method of claim 1 wherein the membrane is phosphocellulose paper.

3. The method of claim 2, wherein said applied force is centrifugal force.

4. The method of claim 3 wherein the enzyme is Protein Kinase A.

5. The method of claim 3 wherein the enzyme is Protein Kinase C.

6. The method of claim 3 wherein the enzyme is a tyrosine kinase.

7. The method of claim 3 wherein the radioactive donor compound is $^{32}$P-ATP.

8. The method of claim 7 wherein the enzyme is Protein Kinase A.

9. The method of claim 7 wherein the enzyme is Protein Kinase C.

10. The method of claim 7 wherein the enzyme is a tyrosine kinase.

11. The method of claim 1, wherein said applied force is centrifugal force.

12. The method of claim 11 wherein the radioactive donor compound is $^{32}$P-ATP.

* * * * *